United States Patent
Ayers et al.

(10) Patent No.: US 8,585,590 B2
(45) Date of Patent: *Nov. 19, 2013

(54) METHOD AND SYSTEM FOR REPRESENTATION OF CURRENT AND HISTORICAL MEDICAL DATA

(75) Inventors: Jonathan W. Ayers, Portland, ME (US); Anestes Fotiades, Portland, ME (US); Robert Brazell, Cape Elizabeth, ME (US); David Dieffenbach, Portland, ME (US)

(73) Assignee: Idexx Laboratories, Inc., Westbrook, ME (US)

( * ) Notice: Subject to any disclaimer, the term of this patent is extended or adjusted under 35 U.S.C. 154(b) by 1233 days.

This patent is subject to a terminal disclaimer.

(21) Appl. No.: 11/733,353

(22) Filed: Apr. 10, 2007

(65) Prior Publication Data

US 2007/0198301 A1 Aug. 23, 2007

Related U.S. Application Data

(63) Continuation-in-part of application No. 11/620,342, filed on Jan. 5, 2007.

(51) Int. Cl.
*A61B 5/00* (2006.01)

(52) U.S. Cl.
USPC .............................................. 600/301; 705/2

(58) Field of Classification Search
USPC .................................. 600/300–301; 705/2–4
See application file for complete search history.

(56) References Cited

U.S. PATENT DOCUMENTS

| | | | | | |
|---|---|---|---|---|---|
| 4,062,568 | A | * | 12/1977 | Schrantz et al. | 283/66.1 |
| 4,315,309 | A | * | 2/1982 | Coli | 705/3 |
| 4,464,122 | A | * | 8/1984 | Fuller et al. | 434/262 |
| 5,423,033 | A | | 6/1995 | Yuen | |
| 5,447,164 | A | | 9/1995 | Shaya et al. | |

(Continued)

FOREIGN PATENT DOCUMENTS

| EP | 0761255 | 3/1997 |
|---|---|---|
| EP | 1839615 | 10/2007 |

(Continued)

OTHER PUBLICATIONS

Fearn et al., "A Chronological Database as Backbone for Clinical Practice and Research Data Management", 2003 Proceedings, Computer-Based Medical Systems, 16th IEEE Symposium, pp. 9-15 (Jun. 26-27, 2003).

(Continued)

*Primary Examiner* — Bill Thomson
*Assistant Examiner* — Bobby Soriano
(74) *Attorney, Agent, or Firm* — McDonnell Boehnen Hulbert & Berghoff LLP

(57) ABSTRACT

A method and system for reporting medical data including both current and past medical results for medical tests performed on a patient is provided. The medical data is output in columns, and the current results and past results of the same medical test are presented in the same row. In this manner, the report is provided in a layout that has rows and columns, so that all current results are presented in one column, and all past results are presented in a separate column. In addition, graphs of the medical results can be displayed to illustrate current and past medical results in a view that allows for trend and comparative diagnosis.

17 Claims, 9 Drawing Sheets

(56) References Cited

U.S. PATENT DOCUMENTS

| | | | |
|---|---|---|---|
| 5,465,378 | A | 11/1995 | Duensing et al. |
| 5,581,460 | A | 12/1996 | Kotake et al. |
| 5,592,945 | A | 1/1997 | Fiedler |
| 5,640,549 | A | 6/1997 | Powsner et al. |
| 5,830,150 | A | 11/1998 | Palmer et al. |
| 5,832,504 | A | 11/1998 | Tripathi et al. |
| 5,941,820 | A | 8/1999 | Zimmerman |
| 6,055,541 | A | 4/2000 | Solecki et al. |
| 6,081,809 | A | 6/2000 | Kumagai |
| 6,889,363 | B2 | 5/2005 | Maloney |
| 6,901,277 | B2 | 5/2005 | Kaufman et al. |
| 6,956,572 | B2 | 10/2005 | Zaleski |
| 6,987,998 | B2 | 1/2006 | Kalgren et al. |
| 7,031,979 | B2 | 4/2006 | Kauffman |
| 7,039,878 | B2 | 5/2006 | Auer et al. |
| 7,059,721 | B2 | 6/2006 | Hayashi et al. |
| 7,069,085 | B2 | 6/2006 | Cao et al. |
| 7,076,436 | B1 | 7/2006 | Ross, Jr. et al. |
| 7,076,492 | B2 | 7/2006 | Campbell et al. |
| 7,113,933 | B1 | 9/2006 | Imholte |
| 2002/0091548 | A1* | 7/2002 | Auer et al. ............ 705/3 |
| 2003/0023461 | A1* | 1/2003 | Quintanilla et al. ......... 705/3 |
| 2003/0036683 | A1* | 2/2003 | Kehr et al. ............ 600/300 |
| 2003/0125983 | A1* | 7/2003 | Flack et al. ............ 705/2 |
| 2003/0144886 | A1* | 7/2003 | Taira ............ 705/3 |
| 2004/0034288 | A1* | 2/2004 | Hennessy et al. ............ 600/300 |
| 2004/0204635 | A1 | 10/2004 | Scharf et al. |
| 2005/0010447 | A1* | 1/2005 | Miyasaka et al. ............ 705/3 |
| 2005/0119534 | A1* | 6/2005 | Trost et al. ............ 600/300 |
| 2005/0234903 | A1 | 10/2005 | Makino |
| 2006/0064020 | A1 | 3/2006 | Burnes et al. |
| 2006/0064325 | A1* | 3/2006 | Matsumoto et al. ............ 705/3 |
| 2006/0206360 | A1 | 9/2006 | Ohta |
| 2006/0241353 | A1* | 10/2006 | Makino et al. ............ 600/300 |
| 2006/0247527 | A1* | 11/2006 | Maruyama ............ 600/443 |
| 2006/0293920 | A1* | 12/2006 | Stroup et al. ............ 705/2 |
| 2007/0073559 | A1* | 3/2007 | Stangel ............ 705/2 |
| 2007/0088525 | A1* | 4/2007 | Fotiades et al. ............ 702/131 |
| 2007/0161870 | A1* | 7/2007 | Abel ............ 600/300 |
| 2007/0198301 | A1* | 8/2007 | Ayers et al. ............ 705/3 |
| 2007/0299316 | A1* | 12/2007 | Haslehurst et al. ............ 600/300 |
| 2009/0118651 | A1* | 5/2009 | Rousso et al. ............ 601/134 |

FOREIGN PATENT DOCUMENTS

| | | |
|---|---|---|
| JP | 200048107 | 2/2000 |
| JP | 2000293594 | 10/2000 |
| JP | 2002306424 | 10/2002 |
| JP | 2004334466 | 11/2004 |
| JP | 2005196661 | 7/2005 |
| JP | 2006338521 | 12/2006 |
| TW | 229281 | 3/2005 |
| WO | WO 2005/087091 | 9/2005 |
| WO | WO 2006/093807 | 9/2006 |

OTHER PUBLICATIONS

Kohler et al., "Application of Interactive Multivariate Data Visualisation to the Analysis of Patient Findings in Metabolic Research", Third International Conference, Knowledge-Based Intelligent Information Engineering Systems, pp. 397-402 (Dec. 1999).

Crowe et al., "Modular Sennsor Architecture for Unobstructed Routine Clinical Diagnosis", 24th International Conference on Distributed Computing Systems Workshops, 2004 Proceedings, pp. 451-453 (Mar. 23-24, 2004).

Maloney et al., "The Clinical Display of Radiologic Information as an Interactive Multimedia Report", J. Digit Imaging, pp. 19-21 (May 1999);12(2 Suppl 1).

Sukuvaara et al., "Intelligent Patient Monitor—Its Function nad User Interface", Computers in Cardiology, pp. 373-376 (Sep. 23-26, 1991).

Portoni et al., "User-Oriented Views in Health Care Information Systems", IEEE Trans Bomed Eng Dec. 2002; 49(12); pp. 1387-1398).

The Heska Lab Reporting System, dated Oct. 14, 2004.

Dozer IDEXX printout, dated May 14, 2005.

Buttons IDEXX printout, dated May 14, 2005.

Powsner, et al. "Graphical Summary of Patient Status", The Lancet, vol. 344, pp. 386-389 (1994).

International Search Report and Written Opinion issued by the European Patent Office for PCT/US2008/050110.

* cited by examiner

| Client: John Hersch | Date: 11/24/2007 | | | | | |
|---|---|---|---|---|---|---|
| Patient: Puddles | Gender: Neutered Male | | | | | |
| Species: Canine | Weight: 11 lbs | | | | | |
| Breed: Labradoodle | Age: 5 years | | | | | 7/23/2006 |
| Test | Result | Reference Range | | Low | Normal | High | Last Run |

VetTest Chemistry Analyzer

| Test | Result | | Reference Range | | | | Last Run |
|---|---|---|---|---|---|---|---|
| BUN | 22 | mg/dL | 7. – 27 | | | | 15 |
| CREA | 1.3 | mg/dL | 0.5 – 1.8 | | | | |
| PHOS | 5.3 | mg/dL | 2.5 – 6.8 | | | | 4.0 |
| CA | 7.7 | mg/dL | 7.9 – 12.0 | LOW | | | 13.1 |
| TP | 5.1 | g/dL | 5.2 – 8.2 | LOW | | | |
| ALB | 2.8 | g/dL | 2.2 – 3.9 | | | | |
| GLOB | 23 | g/dL | 2.5 – 4.5 | LOW | | | |
| ALT | 438 | U/L | 10. – 100. | HIGH | | | 95 |
| ALKP | 1040 | U/L | 23. – 212. | HIGH | | | 300 |
| TBIL | 4.5 | mg/dL | 0.0 – 0.9 | HIGH | | | 1.5 |
| AMYL | 1278 | U/L | 500. – 1500. | | | | 1250 |
| LIPA > | 6000 | U/L | 200. – 1800. | HIGH | | | 1600 |
| GLU | 135 | mg/dL | 74. – 149. | HIGH | | | 89 |

Chem 11 Plus Lipase

| Test | Result | | Reference Range | | | | |
|---|---|---|---|---|---|---|---|
| BUN | 22 | mg/dL | 7. – 27 | | | | |
| CREA | 1.3 | mg/dL | 0.5 – 1.8 | | | | |
| PHOS | 5.3 | mg/dL | 2.5 – 6.8 | | | | |
| CA | 7.7 | mg/dL | 7.9 – 12.0 | LOW | | | |
| TP | 5.1 | g/dL | 5.2 – 8.2 | LOW | | | |
| ALB | 2.8 | g/dL | 2.2 – 3.9 | | | | |
| GLOB | 23 | g/dL | 2.5 – 4.5 | LOW | | | |
| ALT | 438 | U/L | 10. – 100. | HIGH | | | |
| ALKP | 1040 | U/L | 23. – 212. | HIGH | | | |
| TBIL | 4.5 | mg/dL | 0.0 – 0.9 | HIGH | | | |
| AMYL | 1278 | U/L | 500. – 1500. | | | | |
| LIPA > | 6000 | U/L | 200. – 1800. | HIGH | | | |

T4    135  mg/dL

SNAP 4Dx

| Heartworm | positive | | | | | | negative |
| Lyme | negative | | | | | | negative |
| E. Canis | negative | | | | | | negative |
| Annaplasma | negative | | | | | | negative |

Ca

Spec. Gravity

FIGURE 4

METHOD AND SYSTEM FOR REPRESENTATION OF CURRENT AND HISTORICAL MEDICAL DATA

CROSS REFERENCE TO RELATED APPLICATION

This application is a continuation-in-part of U.S. patent application Ser. No. 11/620,342 filed Jan. 5, 2007, which is hereby incorporated by reference in its entirety including all tables, figures and claims.

FIELD OF INVENTION

The present application relates to representations of medical data, and more particularly to graphical and textual displays of current and historical medical data pertaining to a subject undergoing testing.

BACKGROUND

A medical record, health record or medical chart is a systematic documentation of a subject's (human patient or animal) medical history and care. A medical record includes both a physical folder for each individual patient and contains the body of information that comprises the total of each patient's health history. Medical history of a subject is gained by a physician or other healthcare professional by recording physical data or by asking specific questions, either of the patient or of other people who know the patient and can give suitable information, with the aim of obtaining information useful in formulating a diagnosis and providing medical care to the patient.

Medical histories vary in their depth and focus. For example, ambulance paramedics may typically limit their history to important details such as name, history of presenting complaint, allergies etc. In contrast, a psychiatric history can be lengthy and in depth since many details about a patient's life are relevant to formulating a management plan for a psychiatric illness.

Information in a medical record is necessary to provide continuity of care so that all appropriate health care providers have access to the health history. The medical record also serves as a basis for planning patient care, to document communication between health care providers, to assist in protecting legal interests, and to document care and services provided to the subject.

Traditionally, medical records have been written on paper and kept in folders. The folders are typically divided into useful sections, with new information added to each section chronologically as the patient experiences new medical issues. Active records are usually housed at the clinical site, but older records (e.g., those of the deceased) are often kept in separate facilities.

The advent of electronic medical records (EMR) has changed some of the format of medical records, but mainly has increased accessibility of files. Even so, existing formats for viewing medical records can lack the ability to view both current and historical data pertaining to a subject in a display readily accessible for diagnosing the subject.

SUMMARY

Within embodiments disclosed below, a method of reporting medical data is provided.

The method includes receiving current result data of medical tests performed on a patient and outputting the current result data of the medical tests in a layout having rows and columns. The method also includes outputting previous result data of medical tests performed on the same patient in the layout in a separate column, so that previous result data and current result data of the same medical test are in the same row in the layout.

The method may additionally include receiving a request to output a graph of medical data pertaining to a selected medical test and outputting the graph of the medical data in the layout. The graph includes data points corresponding to current result data and previous result data of the selected medical test and an axis of the graph corresponds to a date of the current result or the previous result data point. The method can also include outputting a graphical indicator for each medical test that indicates whether the current result data of the medical test is low, normal or high, wherein the graphical indicator is a slidebar that illustrates a measurement value for the medical test and the graphical indicator is output in the layout in a column between the current result data and the previous result data so that the previous result data, the current result data and the graphical indicator of the same medical test are in the same row in the layout. Alternatively, graphical methods other than the slidebar can be used to represent medical information for which a slidebar is not the most effective means of visually communicating the information. Furthermore, the method may also include outputting a range of reference data pertaining to each medical test in the layout in a column between the current result data and the previous result data so that the previous result data, the current result data and the range of reference data of the same medical test are in the same row in the layout, wherein the range of reference data defines values for results of the medical test pertaining to a low and a high result.

The method may also include outputting standard deviation information for the data via text and/or graphical means, and may provide a one-touch method for triggering the automatic generation of a graph that includes current and historical results data with or without standard deviation information.

In another embodiment, a graphical interface for displaying medical data is provided that includes medical data pertaining to current results of medical tests in a layout having rows and columns and medical data pertaining to previous results of the medical tests in the layout in a column by the current results, so that previous results and current results of the same medical test are in the same row in the layout. The graphical interface also includes a graph in the layout illustrating medical data for a medical test in which the graph includes data points corresponding to current result data and previous result data.

In still another embodiment, a computer readable medium that has program code recorded thereon for execution on a computer to provide a report of medical data is provided. The medium includes a first program code for outputting medical data pertaining to current results of medical tests in a layout having rows and columns, and a second program code for outputting medical data pertaining to previous results of the medical tests in the layout in a column, so that previous results and current results of the same medical test are in the same row in the layout.

In other embodiments, a method of reporting medical data includes receiving current result data of medical tests performed on a patient and outputting the current result data of the medical tests in a graph. The method also includes outputting previous result data of the medical tests performed on the patient in the graph, so that the previous result data and the current result data of the medical tests are associated. The medical tests may be selected from a group of tests relevant to kidney or liver function.

These and other aspects will become apparent to those of ordinary skill in the art by reading the following detailed description, with reference where appropriate to the accompanying drawings. Further, it should be understood that the embodiments noted herein are not intended to limit the scope of the invention as claimed.

BRIEF DESCRIPTION OF FIGURES

FIG. 4 is an example illustration of a graph generated using a method of the present invention.

DETAILED DESCRIPTION

The present application provides a manner of reporting medical data including both current and past medical results for medical tests performed on a patient in a display readily accessible for diagnosing the subject. In addition, graphs of the medical results can be displayed to illustrate current and past medical results in a view that allows for trend and comparative diagnosis.

Figure 1:
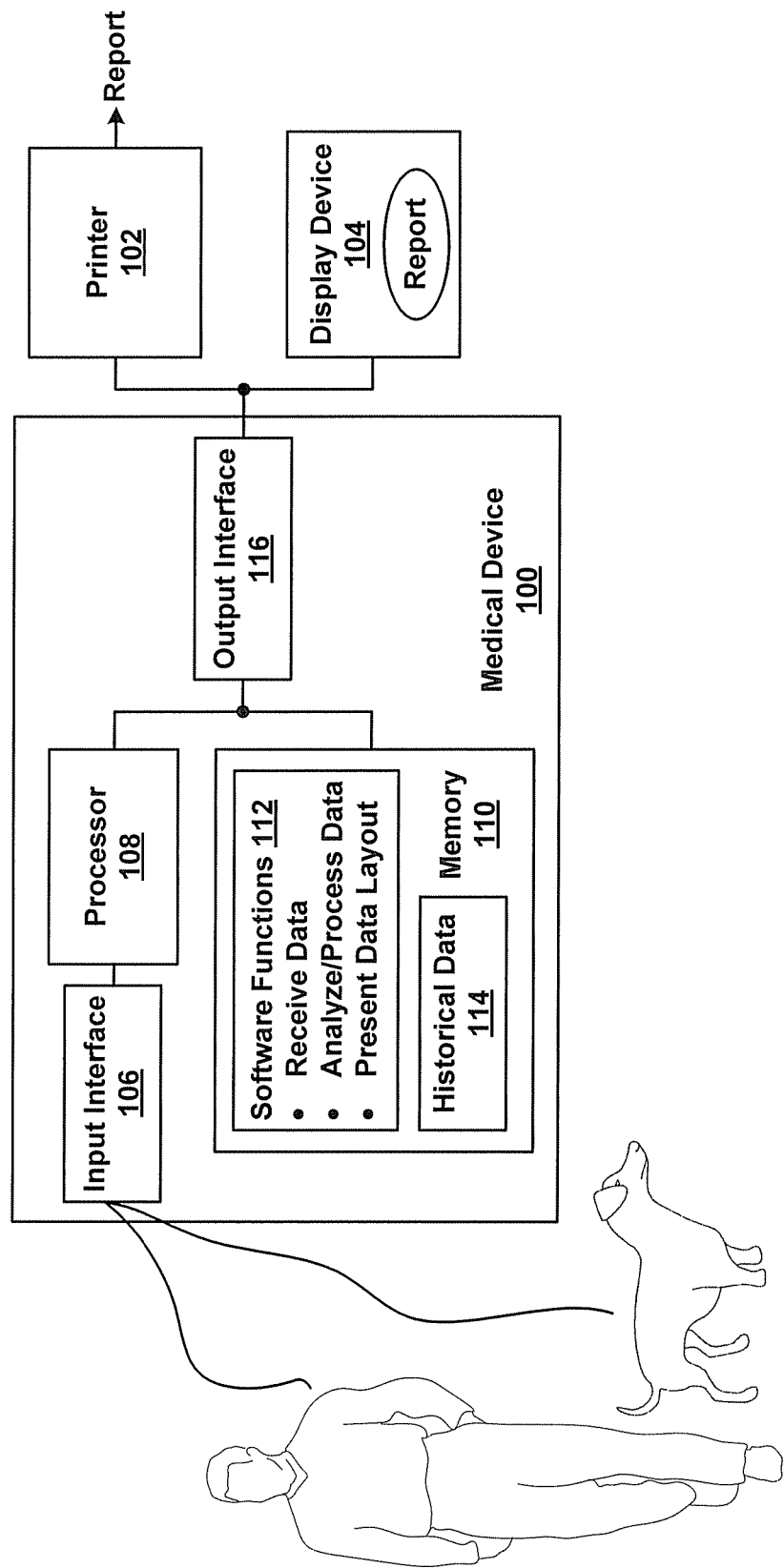
FIG. 1 is a block diagram of an example system for reporting medical data.

Referring now to the figures, FIG. 1 is a system for reporting medical data. The system includes a medical device 100 that outputs to a printer 102 and a display device 104 (e.g., a computer monitor). The medical device 100 includes an input interface 106 that receives medical readings from a patient, such as a person or animal, and sends the readings to a processor 108. The input interface 106 may also receive inputs from a user including instructions for processing the medical readings. The processor 108 accesses memory 110 to execute any of the software functions 112 stored therein, such as to receive the medical readings, analyze and process the readings, and to present the data to the printer 102 or the display device 104, for example. The processor 108 further accesses the memory 110 to retrieve stored historical data 114, or past medical results, and may combine the historical data 114 with the received medical readings to be output to the printer 102 or the display device 104 through an output interface 116. A system bus or an equivalent system may also be provided to enable communications between various elements of the medical device 100, the printer 102 or the display device 104.

The medical device 100 may be of the type provided by IDEXX Laboratories, Inc., of Westbrook, Me., USA. For example, the medical device 100 may be one of those within the IDEXX VetLab® Suite that delivers information on blood chemistries, proteinuria, electrolytes, hematology, endocrinology and blood gases. Such devices include the VetTest® instrument, the LaserCyte® hematology analyzer, the VetLyte® electrolyte analyzer, or the VetStat® blood gas analyzer, for example.

The medical device 100 generally can range from a handheld device, laptop, or personal computer to a larger computer such as a workstation and multiprocessor. The medical device 100 may also include an input device, such as a keyboard and/or a two or three-button mouse, if so desired. One skilled in the art of computer systems will understand that the example embodiments are not limited to any particular class or model of computer employed for the medical device 100 and will be able to select an appropriate system.

As such, the medical device 100 generally includes a central processing unit, a memory (a primary and/or secondary memory unit), an input interface for receiving data, an input interface for receiving input signals from one or more input devices (for example, a keyboard, mouse, etc.), and an output interface for communications with an output device (for example, a monitor). In general, it should be understood that the medical device 100 could include hardware objects developed using integrated circuit development technologies, or yet via some other methods, or the combination of hardware and software objects that could be ordered, parameterized, and connected in a software environment to implement different functions described herein. Also, the hardware objects could communicate using electrical signals, with states of the signals representing different data. It should also be noted that the medical device 100 generally executes application programs resident at the medical device 100 under the control of the operating system of the medical device 100.

In addition, the input interface 106 may include any standard medical interface for collecting desired medical readings from a patient, either human or animal. Further, the input interface 106 and the output interface 116 may be any standard computer interface and may include, for example, a keyboard. However, other interfaces may be used as well. Moreover, the memory 110 may include main memory and secondary storage. The main memory may include random access memory (RAM). Main memory can also include any additional or alternative memory device or memory circuitry. Secondary storage can be provided as well and may be persistent long term storage, such as read only memory (ROM), optical or magnetic disks, compact-disc read only memory (CD-ROM), or any other volatile or non-volatile storage systems. The memory 110 may include more software functions 112 as well, for example, executable by the processor 108 to record signals from a patient and interpret the signals as medical readings. The software functions 112 may be provided using machine language instructions or software with object-oriented instructions, such as the Java programming language. However, other programming languages (such as the C++ programming language for instance) could be used as well.

It will be apparent to those of ordinary skill in the art that the methods described herein may be embodied in a computer program product that includes one or more computer readable media, as described as being present within the medical device 100. For example, a computer readable medium can include a readable memory device, such as a hard drive device, a CD-ROM, a DVD-ROM, or a computer diskette, having computer readable program code segments stored thereon. The computer readable medium can also include a communications or transmission medium, such as, a bus or a communication link, either optical, wired or wireless having program code segments carried thereon as digital or analog data signals.

Furthermore, the processor 108 may operate according to an operating system, which may be any suitable commercially available embedded or disk-based operating system, or any proprietary operating system. The processor 108 may comprise one or more smaller central processing units, including, for example, a programmable digital signal processing engine. The processor 108 may also be implemented as a single application specific integrated circuit (ASIC) to improve speed and to economize space.

It should be further understood that this and other arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

Figure 2:
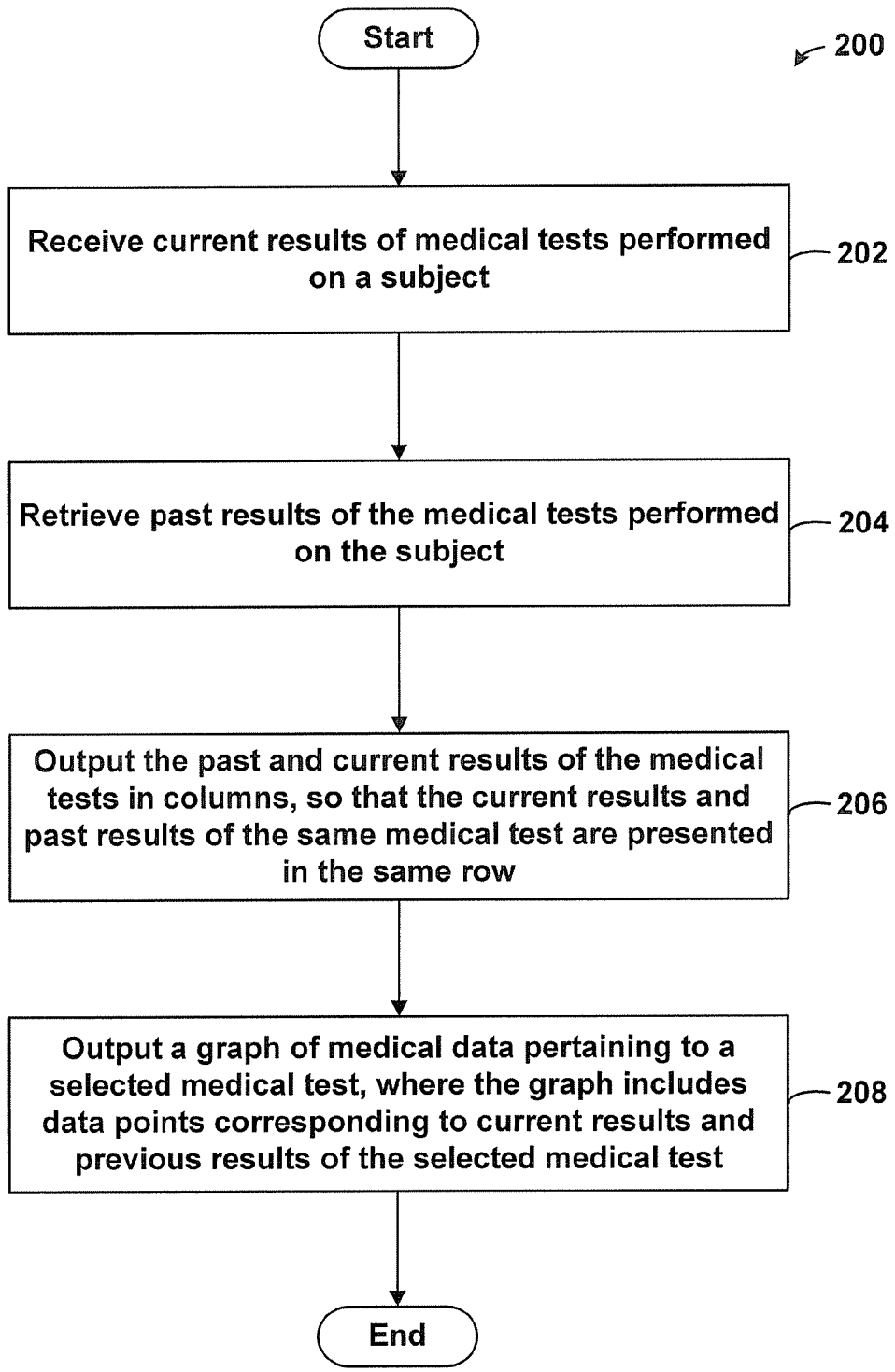
FIG. 2 is a flowchart illustrating exemplary functional steps of a method executable by a processor to output a medical data report.

The medical device 100 operates to output a medical report to the display device 104 and the printer 102. Alternatively, the output can include a transmission (e.g. fax, e-mail) to a remote location (such as from a reference laboratory to a clinic). The report includes the historical data 114 of a patient along with the current medical readings of the same patient. FIG. 2 is a flowchart illustrating functional steps of a method 200 executable by the processor 108 to output the report. It should be understood that each block in this flowchart (and within other flow diagrams presented herein) may represent a module, segment, or portion of computer program code, which includes one or more executable instructions for implementing specific logical functions or steps in the process. Alternate implementations are included within the scope of the example embodiments in which functions may be executed out of order from that shown or discussed, including substantially concurrently or in reverse order, depending on the functionality involved, as would be understood by those reasonably skilled in the art of the described embodiments.

In FIG. 2, initially, current results of medical tests and/or other information relating to a subject are received into the medical device 100, as shown at block 202. The processor 108 will then retrieve past results of medical tests performed on the same subject from the historical data 114, as shown at block 204. The past medical results may include only the most recent results, the results over a prior period of time, selected past medical results, or all the past results pertaining to the subject under test. Furthermore, the past medical results may include only results pertaining to the medical tests currently performed, all results for all medical tests performed on the subject, or a selected amount or type of results for medical tests that have been performed on the subject. Any combination of number of results, or type of results may be retrieved.

Next, the processor 108 will output to the printer 102 and/or display device 104 the past and current results of the medical tests in columns, so that the current results and past results of the same medical test are presented in the same row, as shown at block 206. In this manner, the report is provided in a layout that has rows and columns, so that all current results are presented in one column, and all past results are presented in a separate column. Further, past and current results of the same medical test performed on the same subject are presented in the same row.

Thus, the processor 108 may output a graphical user interface (GUI) to the display device 104 that shows the medical data. The processor 108 may execute the software functions 112 to create the data layout, and additional charts or graphs, on the display device 104. The display device 104 illustrates the graphical user interface, which enables a user to analyze medical data in a visual display and accepts user inputs/instructions to illustrate selected data in a desired manner.

The graphical user interface (GUI) may be of a standard type of user interface allowing a user to interact with a computer that employs graphical images in addition to text to represent information and actions available to the user. Actions may be performed through direct manipulation of graphical elements, which include windows, buttons, menus, and scroll bars, for example.

In addition, the processor 108 may optionally output a graph of medical data pertaining to a selected medical test, as shown at block 208. The graph will include data points corresponding to current and previous results of the selected medical test. The graph may be included within the same medical report as the current and historical medical data, or within a separate report as well. In the instance that the report is output to the display device 104, the graph may be included within a separate "pop-up" window in the GUI.

A graph is used to present the current and previous medical results in a visual form. A graph is produced by plotting medical data points and joining successive points with a line. For example, the medical data may be plotted such that a y-axis of a graph represents units pertaining to a specific medical test and an x-axis of a graph represents the date of the medical test, so that by joining successive data points of the graph, a trend in the patient's test results can be visually identified.

Many different types of graphs may be produced using the medical data, such as (but not limited to) a bar graph, a line graph, pie graphs, etc. A bar graph may be used to show relationships between multiple medical tests. The two tests being compared do not need to affect each other. This form is one way to show differences in test results between two tests. A line graph may used to show continuing data, such as how a patient's test results vary over time. A line graph provides a clear manner to view how a patient's test results are going by the rises and falls in the line graph. The line graph can be used to show the effect of an independent variable on a dependent variable, such as for example, the medical test results of a patient over time. A circle graph may be used to show how a part of something relates to the whole, such as for example, to indicate different medical tests performed over time. Still other graphical or visual data structures may also be presented to visually display the medical test result data of a patient.

Figure 3:
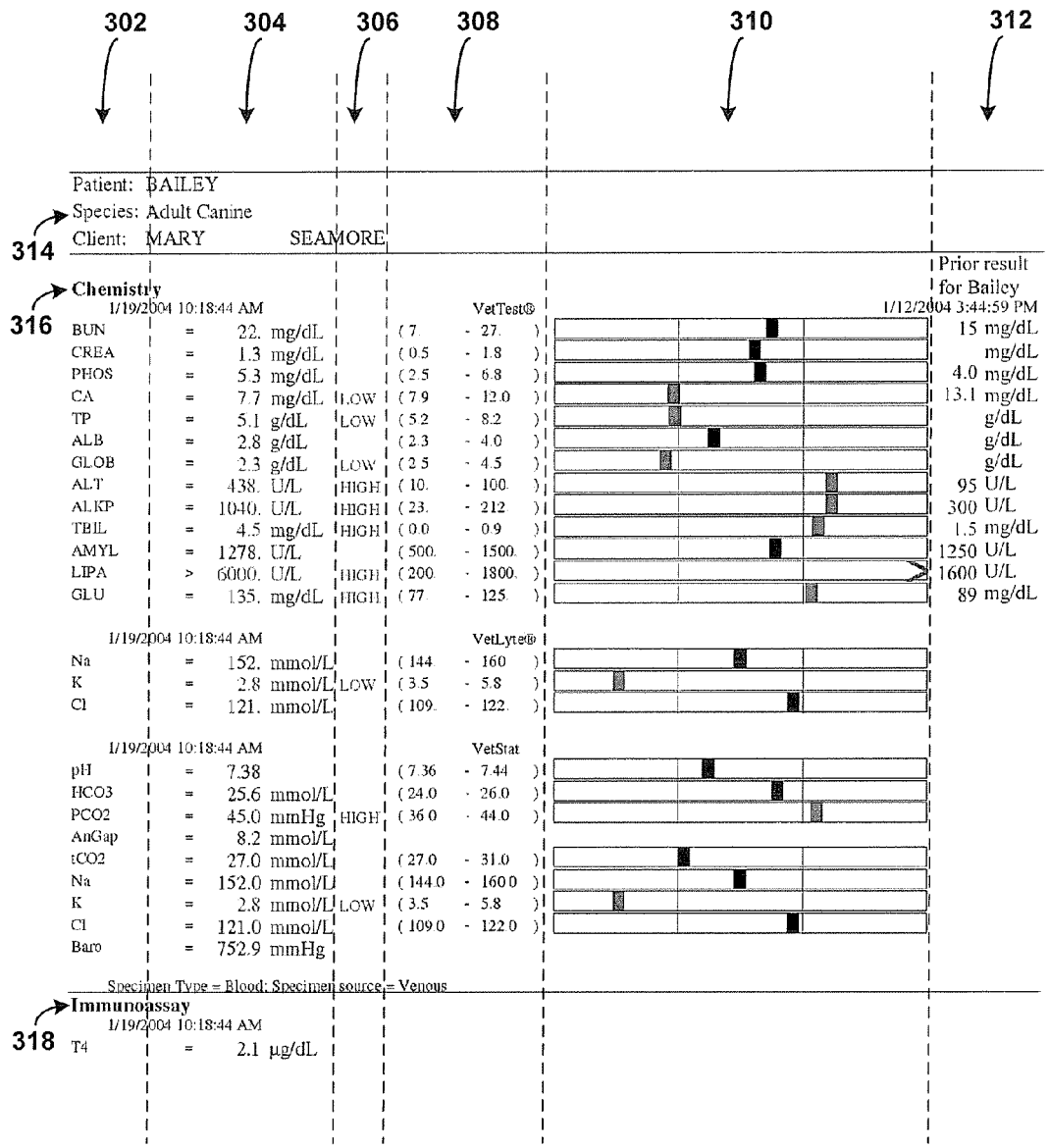
FIG. 3 illustrates one example output of a medical data report.

FIG. 3 illustrates one example output of the report. As shown, the report presents data within columns 302-312. Data within column 302 includes a name of the compound being tested, and data within column 304 includes the current result of the medical test with a numerical value and unit. Data within column 306 includes a textual indicator identifying if the current result is "HIGH" or "LOW" with regard to a range of reference data pertaining to the medical test that defines values for results of the medical test pertaining to a low and a high result. The range of reference data is included within column 308. The indicators in column 306 may only be shown when the current result exceeds the critical high or critical low defined within the range of reference data, for example.

A result may be considered abnormal if the result falls outside of the range of reference data. When a result is abnormal and displayed on a color screen, the test name, result data, units and high/low indicator may be displayed in a color distinguishable from the other results. When a result is abnormal and displayed on a black and white screen or printout (e.g. faxed results), the test name, result number, units and high/low indicator may appear in bold text. This provides a non-color dependant approach to indicating abnormal results. Other distinguishing visual characteristics may be used as well.

The report further includes graphical indicators in column 310, which are slidebars that include marks to illustrate where the test result falls within a predetermined range and whether the current result is high or low. The slidebars may also include additional marks either shadowed or otherwise differentiated to illustrate whether previous results have been high or low for the same medical test performed on the same subject. The slidebars may, for example, occupy 30% of the width used to display the report, not including margins. Other types of graphical indicators may be used as well, such as a standard odometer type, a vertical slidebar, or color indicators, for example. In addition, the slidebar marks can include lateral indicia, such as attached dash marks (not shown), that relate to the standard deviation of the value being presented. The magnitude of the standard deviation can be preprogrammed into memory. Displaying one or more marks with integral standard deviation values will enable the physician to more easily make a visual determination if the medical information (e.g., test result) is out of a predetermined range.

A majority of margin space for a report is concentrated on the right-hand side of the report. This provides an area for the medical staff to write if the report is printed out on paper. A portion of this space can also be used to present the previous results for medical tests performed on the same subject, as shown in column 312. Of course, the previous result data column may be placed in other positions within the layout of the report. The previous results may include only the most recent test event that includes any of the data series shown on the report pertaining to the current results, for example, and will display the previous results in the additional column of data. As a subsequent expansion of this feature, the additional column could include data that is a composite of the most recent results from multiple test events corresponding to the tests currently performed. As mentioned, the previous results data column 312 may include data from any combination of a number of previous results, age of the results, or type of results.

The report may also include patient identification, as shown at 314, and test identification within section headers, as shown at 316 and 318. Also, information pertaining to individual tests, such as test 316 and 318, is grouped together in adjacent rows as shown in the report. The tests results pertaining to "Chemistry" are positioned in adjacent rows, while the tests pertaining to "Immunoassay" are shown in a separate section of the layout. The section headers may be the name of the medical test or the name of the instrument recording the medical readings, for example.

The data in the report is in a layout such that all current result data is contained within one column (e.g., column 304) and all previous result data is contained within a separate column (e.g., column 312), while previous result data and current result data of the same medical test are presented in the same row in the layout. In this manner, the current result data can be compared with the previous result data by scrolling from left to right across the report. Thus, the data can be presented on the report in a table structure or format, so that all data within a given column corresponds to results collected on the same day, and all data within a given row corresponds to results collected from the same medical test. Using this structure, medical data pertaining to a specific result may be contained within a cell of the table.

Further, in the instance in which all previous result data in column 312 pertains to one testing date, additional columns may be provided to the right of column 312, if space is available, to provide data from other previous testing dates.

Dates and times corresponding to the date and time for performing the current tests to obtain the current results and for when the previous results were obtained are also included in the report. The format for Date/Time data will be controlled by the localization settings of the application. As a general rule, Date/Time display may be no more detailed than is necessary to make a meaningful distinction, for example. The Date/Time data is shown in the column pertaining to the previous result, as well as in the column pertaining to the current result data. Alternatively, asterisks and other superscripted characters can be used to tie the results to the Date/Time for the test events listed in a footer or comment area.

The report may additionally include other information or graphics. For example, the report may include charts or graphs that illustrate trends of the medical data over time. FIG. 4 illustrates an example output of the report with two graphs for two data series, e.g., Ca and Specific Gravity. A user may select data to be output on the report in the graph. Alternatively, graphs may be automatically generated and output on the report for any single data series based on a set of predetermined rules. As an example of a graph generating rule set, a graph may be automatically included in a report if the current result is abnormal and at least two previous data points for that series exist. For example, in the report shown in FIG. 4, the current results for Ca are outside of the reference range, and thus a graphical representation of the results for testing of Ca over the past seven years is included within the report.

An auto-generated graph will include proportional time scales with time markers determined by a proportional division of the time when data points were collected, and a y-axis divided into thirds with the middle third representing the normal range to follow the standard established for slidebars. Data points corresponding to abnormal or out of reference range may be displayed in red.

The graphs are shown at the bottom of the report, however, the graphs may be positioned elsewhere in the report as desired. The graphs are positioned outside of the data table structure containing the medical results, but within the layout of the report.

The report in FIG. 4 illustrates both current and historical medical data in a column format to allow for a comparison of the data in a textual format, as well as current and historical data in a graphical representation to allow for a comparison of the data in an illustrative format. In addition, the medical report allows for years of medical data to be presented in a compressed format onto one page and allows enough detail to show multiple trends within multiple medical tests for a patient.

A user may indicate to the system that an additional graph is required by using a cursor to select a slidebar or row of data of interest, or by moving a cursor over a slidebar of interest to cause a window with the current/historical data on a graph to pop up or otherwise appear layered over the current information on the screen or other display device.

Figure 5:
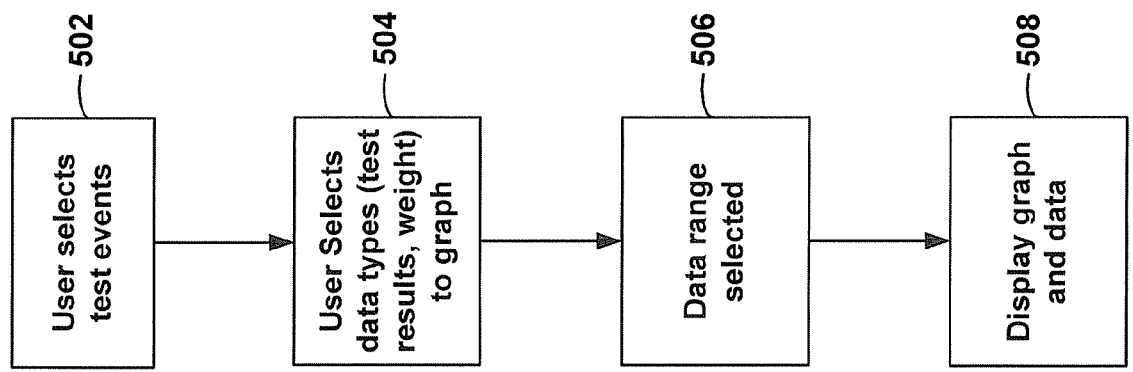
FIG. 5 is a flowchart illustrating exemplary functional steps for generating a graph of medical data for presentation in a report.

FIG. 5 is a flowchart illustrating functional steps for manually generating a graph of the medical data for presentation in the report (as opposed to automatic graph generation, described above and below). Initially, a user of the medical device will select test events for which a graph is desired, as shown at block 502. For example, a user will select one or more test events from the full range of data recording events in the patient's record to display a graph that includes the current results and past results as data points. Next, a user selects data series to be graphed, such as test results pertaining to a certain weight or blood chemistry level, for example, as shown at block 504. Following, a data range from which data of the current results and past results are chosen is selected to be graphed (preferably automatically though software), as shown at block 506. Last, a graph is generated and displayed, as shown at block 508.

The graphs will include the current and past medical data as data points. One axis of the graph will be the units corresponding to the medical data, and the other axis will be the date at which the medical data was recorded and may only include month and year or whatever value is needed to differentiate the data points from one another.

Figure 6:
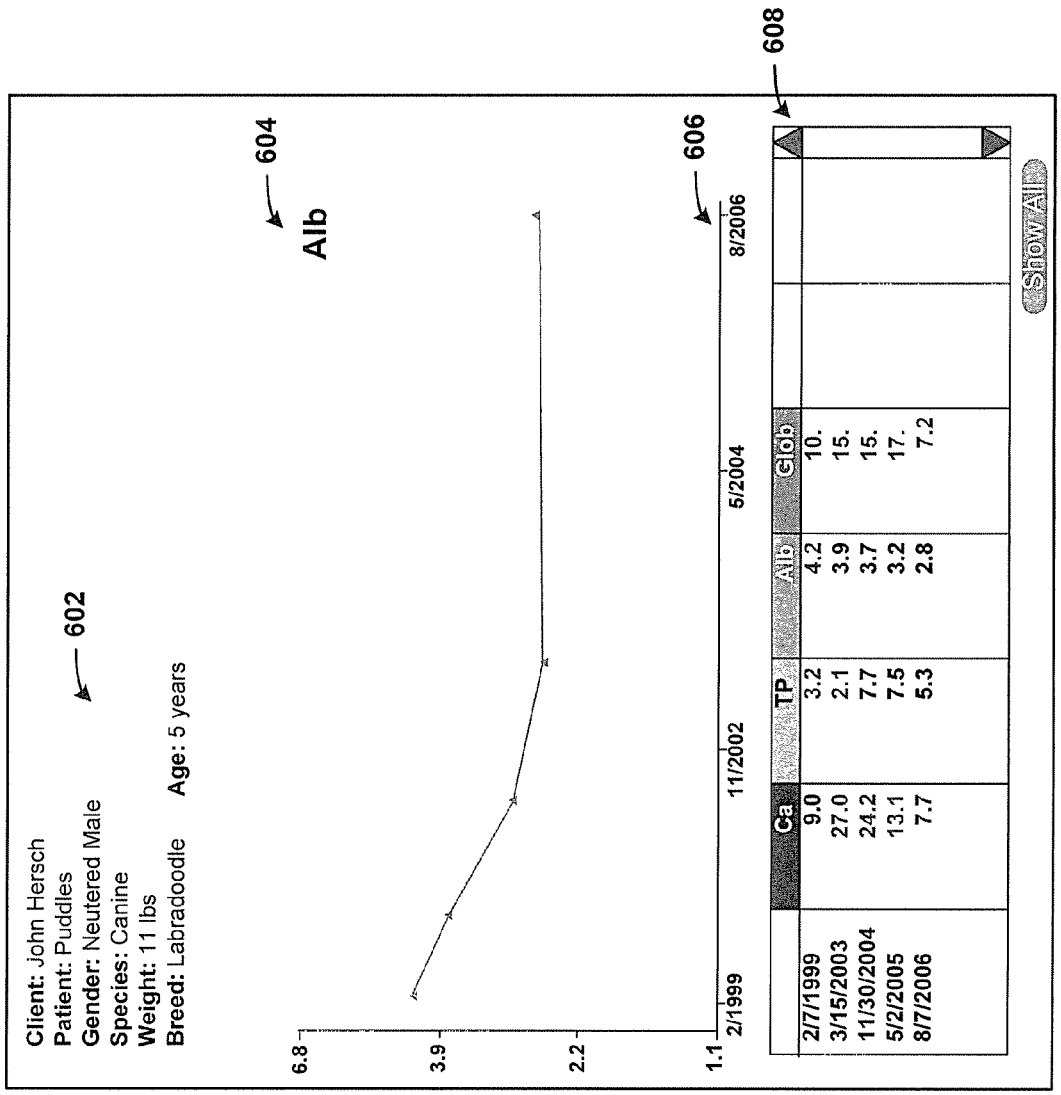
FIG. 6 is another example illustration of a graph generated using the method of the present invention.

FIG. 6 is an example illustration of a graph generated using the method shown in FIG. 5. The graph may include a header 602 with patient information, and a title 604 to indicate the test event that was selected, e.g., Alb. An x-axis 606 displays the date of the data point. First and last date/time markers are determined by the date/time of the earliest and latest test events. The two middle markers are calculated to divide the x-axis into four equal length segments. Only as much specificity as is needed to differentiate all four markers is displayed, for example. If all test events occurred over the span of four weeks, a day/month/year may be shown. If all test events occurred within a single day, a day/month/year and hour/minute may be shown. Alternatively, a date may be shown on the x-axis corresponding to each data point to indicate the specific day at which the medical data at the data point was collected.

Thus, the x-axis may use a non-linear time-scale, or a linear time-scale depending on the existing data points. The most historic data point will be plotted nearest the y-axis, with time progressing from left to right across the x-axis. Alternatively, when the interface is localized for a right to left reading culture the orientation of the x-axis may be reversed.

The y-axis can be divided into any portioned segments as desired. As shown, the y-axis is divided into thirds and shows a relative scale for the data series. The graph may also include a table 608 that textually shows the data points (result and date recorded) for the test that is graphed, as well as data for other tests not graphed. A user may select one of the data series corresponding to a particular test to update the graph with the data points for the data series. As shown, the data points for the test corresponding to Alb are graphed. Alternatively, the information in the columns and rows of table 608 can be switched, i.e. the dates can be column headers and each row can represent particular medical parameters.

Data within the table may be color coded using red/black to indicate abnormal/normal results in a manner that is consistent with the report format without the need to display reference ranges. For example, data shown in red may be interrupted as results out of a reference range. In addition, the column headings may be color coded corresponding to the color used to graph the data to act as a legend for the graph.

Figure 7:
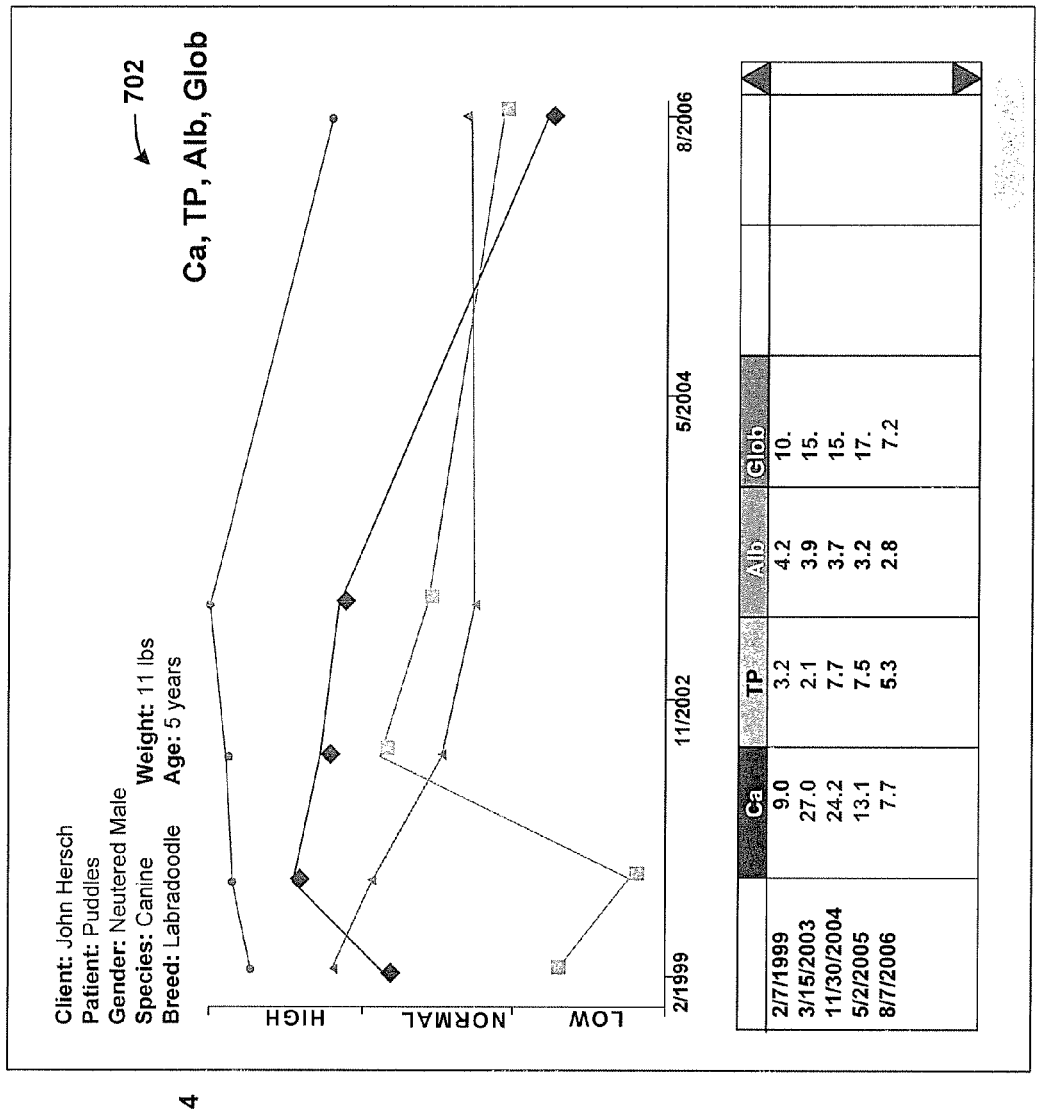
FIG. 7 illustrates another example output of a medical data report.

In addition, the graph may display multiple trends, as shown in FIG. 7. The graph function may be set up to allow a user to choose multiple data series to graph. A user may select any data series for which there are at least two test events that contain a measurement, however, there is no limit to the number of testing events that may be graphed. The graph in FIG. 7 illustrates four trends for the data series corresponding to the tests for Ca, TP, Alb, and Glob as shown in title 702.

When multiple trends are selected to be graphed, distinguishable data point indicators 704 may be used for each data series so that the combination of color and shape can provide a differentiation for users. Also, if there is room (e.g. taking into account legibility and non-interference with graphical information), numerical values of particular data points can be displayed on the graph (e.g. the actual Ca, TP, Alb and Glob values can be placed next to their respective data points if a predetermined amount of room is available). In addition, the descriptor for each set of data can be placed in proximity to its respective plot to aid the user in identifying the particular parameter while looking at the graph. The graph display may also include a button to allow a user to select all the data to be graphed as shown in FIGS. 6 and 7.

Figure 8:
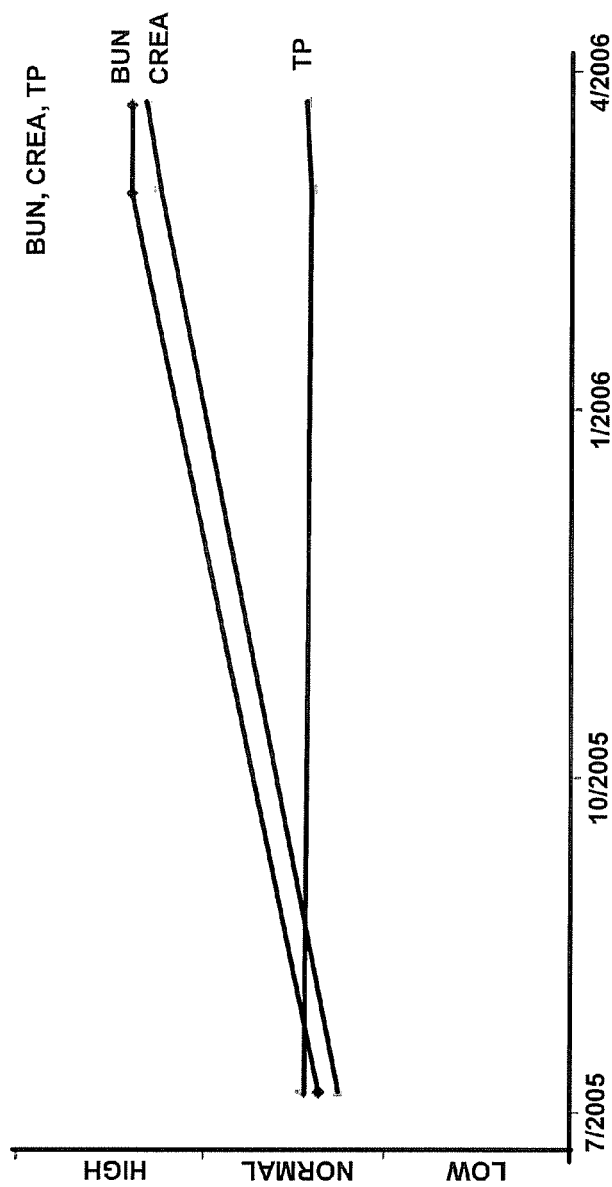
FIG. 8 illustrates another example output of a medical data report.

FIG. 8 illustrates another example of a graph generated using the method described herein. FIG. 8 illustrates medical data for blood urea nitrogen (BUN), creatinine (CREA) and TP test results in both graphical and table format. Unlike the examples FIGS. 6 and 7, in this particular embodiment, the table has dates as columns headers and corresponding medical test result data in rows. And, similar to the example graph shown in FIG. 7, the y-axis is denoted with low, normal and high general levels relating to the test results as characterized by reference data rather than actual magnitudes of the test results.

Figure 9:
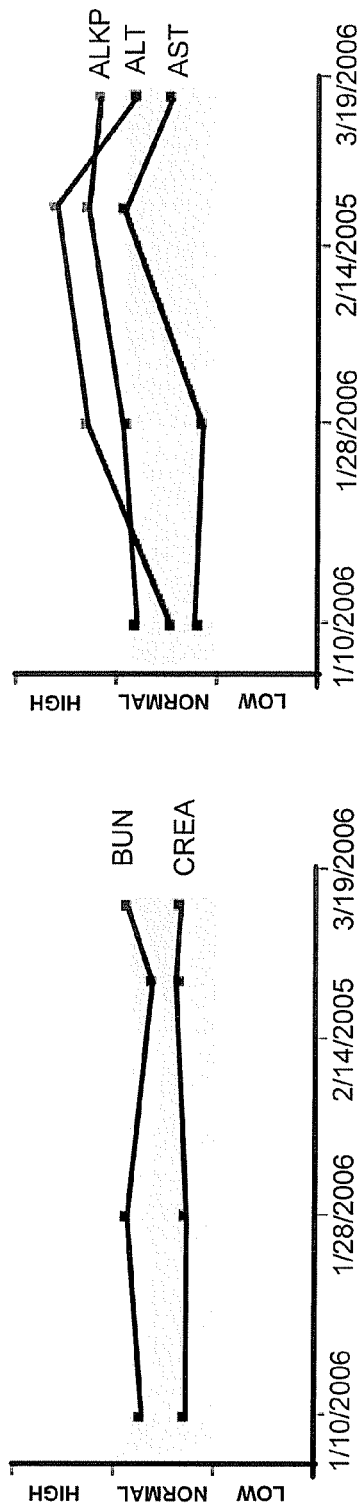
FIG. 9 illustrates another example output of a medical data report including current and historical non-steroidal anti-inflammatory drug (NSAID) monitoring panel data (e.g., ALKP, ALT, AST, BUN and CREA).

FIG. 9 illustrates another example of multiple trend data shown using both the column format and the graphical format. In particular, FIG. 9 illustrates multiple trend data relating to five tests useful for monitoring non-steroidal anti-inflammatory drug (NSAID) therapy that may adversely affect a patient's liver and/or kidney function. Those tests include alkaline phosphatase (ALKP), alanine aminotransferase (ALT) and aspirate aminotransferase that are tests relevant to monitoring liver function, and blood urea nitrogen (BUN) and creatinine (CREA) that are tests relevant to monitoring kidney function. It is desirable to determine baseline values for these tests (or any combination thereof) prior to initiating NSAID therapy and then monitoring test values during NSAID therapy. Once a patient is identified as being in an NSAID therapy program, historical and current test data can be automatically generated for easy and immediate monitoring. The medical test reporting methods disclosed herein are suited for providing the medical practitioner with both current and historical data in a convenient and diagnostically relevant manner. Whether NSAID or any other therapy is being administered (e.g. chemotherapy, antibiotics, antifungals, etc.) the present application provides a tool for the physician to proactively determine if a medication is causing harmful side effects and, if so, to either stop or change the treatment before significant damage occurs.

The present embodiments described herein may be applied to many different types of medical data and medical tests. Data that may be incorporated into the structured reports of the present application in addition to or rather than data content discussed above include ALB (Albumin), ALKP (Alkaline Phosphatase), ALT (Alanine Aminotransferase), AMYL (Amylase), AST, BUN (Urea Nitrogen), Ca (Calcium), CHOL (Cholesterol), CK, CREA (Creatinine), GGT (Gamma GT), GLU (Glucose), LAC, LDH, LIPA (Lipase), Mg (Magnesium), $NH_3$, PHOS (Inorganic Phosphate), TBIL (Total Bilirubin), TP (Total Protein), TRIG (Triglicerides), URIC (Uric Acid), NSAID (Non-steroidal Anti-inflamatory drug) parameter monitoring, UPC ratio, Anion Gap, Sodium, Potassium, Chloride, pH, $PCO_2$, $HCO_3$, $tCO_2$, tHb, $SO_2$, $PO_2$, hematology parameters, T4, bile acids cotisol, pancreatic lipase, height, weight, dental information, cardiac markers (e.g., Pro-ANP, ANP, Pro-BNP, BNP, Troponin), Attitude Score, and patient's temperature, EKG data, just to name a few. Any combination of the described data may be output within the structure of the report described herein. Moreover, any combination of graphical and textual data may be output within the report.

Note that while the present application has been described in the context of a fully functional medical data reporting system and method, those skilled in the art will appreciate that the mechanism of the present application is capable of being distributed in the form of a computer-readable medium of instructions in a variety of forms, and that the present application applies equally regardless of the particular type of signal bearing media used to actually carry out the distribution. Examples of such computer-accessible devices include computer memory (RAM or ROM), floppy disks, and CD-ROMs, as well as transmission-type media such as digital and analog communication links. The mechanism also applies to output on paper.

The terms "test data", "test results", "result data", "medical data", "medical tests", "medical information" (and the like) relate to any information a medical practitioner might record with respect to a particular patient. This information can include, for example, physical characteristics (such as height and weight), physical observations (such as coughing, sneezing, cuts, bruises, limping, skin disorders and dental matters) and physiological tests (such as blood tests, fecal tests and urine tests).

It is intended that the foregoing detailed description be regarded as illustrative rather than limiting, and it is intended to be understood that the following claims including all equivalents define the scope of the invention.

What is claimed is:

1. A medical device, comprising:
   an input interface for receiving current result data of medical tests performed on a patient;
   a processor; and
   memory having stored therein instructions executable by the processor to perform functions of:
      creating an output of the current result data of the medical tests in a layout having rows and columns;
      retrieving from the memory stored previous result data of medical tests performed on the same patient;
      providing the stored previous result data of the medical tests performed on the patient in the layout in a separate column adjacent to margin space of the layout, so that the previous result data and the current result data of the same medical test are in the same row in the layout;
      providing a numerical range of reference data pertaining to each medical test in the layout in a column between the current result data and the previous result data so that the previous result data, the current result data, and the numerical range of reference data of the same medical test are in the same row in the layout, wherein the numerical range of reference data defines values for results of the medical test pertaining to a low and a high result with respect to known results for a patient; and
      outputting the layout to a graphic user interface,
   wherein the medical tests are selected from a group of tests relevant to kidney or liver function.

2. The medical device of claim 1, wherein the instructions are further executable by the processor to perform the functions comprising:
   identifying instances in which a current result of the medical test is abnormal and at least one previous result exists for the medical test; and
   providing in the layout data points including the abnormal current result and the at least one previous result.

3. The medical device of claim 1, wherein the instructions are further executable by the processor to perform the functions comprising:
   indicating a type of instrument used to perform each medical test; and
   indicating within each row of result data in separate columns the following information: a type of test performed, the current result data, the previous result data, the numerical range of reference data that defines values for results of the medical test pertaining to the low and the high result, and a graphical indicator that indicates whether the current result data of the medical test is low, normal or high.

4. The medical device of claim 1, wherein the instructions are further executable by the processor to perform the functions comprising:
   providing a graphical indicator for each medical test that indicates whether the current result data of the medical test is low, normal or high, wherein the graphical indicator is a slidebar that illustrates a measurement value for the medical test, wherein the graphical indicator is output in the layout in a column between the current result data and the previous result data so that the previous result data, the current result data and the graphical indicator of the same medical test are in the same row in the layout.

5. The medical device of claim 4, wherein the instructions are further executable by the processor to perform the functions comprising also outputting on the graphical indicator for each medical test whether the previous results of the medical test have been low, normal or high.

6. The medical device of claim 1, wherein the instructions are further executable by the processor to perform the functions comprising providing a textual indicator that indicates whether the current result data is out of the numerical range of reference data.

7. The medical device of claim 1, wherein the instructions are further executable by the processor to perform the functions comprising transmitting the layout to a remote location.

8. The medical device of claim 1, wherein the function of outputting the previous result data of the medical tests performed on the patient in the layout, so that the previous result data and the current result data of the medical tests are associated comprises outputting a printed document.

9. The medical device of claim 1, wherein the function of outputting the previous result data of the medical tests performed on the patient in the layout, so that the previous result data and the current result data of the medical tests are associated comprises outputting the layout on a computer display.

10. The medical device of claim 1, wherein the instructions are further executable by the processor to perform the functions comprising if a current or previous result data of a medical test is abnormal, outputting data pertaining to the current or previous result data in a color different from normal results.

11. The medical device of claim 1, wherein the medical tests are selected from the group of tests consisting of alkaline phosphatase (ALKP) tests, alanine aminotransferase (ALT) tests, aspirate aminotransferase (AST) tests, blood urea nitrogen (BUN) tests and creatinine (CREA) tests.

12. The medical device of claim 1, wherein the medical tests comprise alkaline phosphatase (ALKP) tests, alanine aminotransferase (ALT) tests, aspirate aminotransferase (AST) tests, blood urea nitrogen (BUN) tests and creatinine (CREA) tests.

13. The medical device of claim 1, wherein the layout is of a form selected from the group consisting of a bar graph, a line graph, and a pie graph.

14. The medical device of claim 1, wherein the layout is in a form of a table structure with data in a given column corresponding to results collected on the same day, and data within a given row corresponding to results collected from the same medical test.

15. The medical device of claim 1, wherein the instructions are further executable by the processor to perform the functions comprising providing in the layout a graph including illustrations indicating both the current result data and the previous result data.

16. The medical device of claim 1, wherein the instructions are further executable by the processor to perform the functions comprising:
- determining if the current result data of the medical test is abnormal;
- determining that at least two previous result data points exist for the same medical test; and
- providing in the layout a graph including illustrations indicating both the current result data and the previous result data.

17. The medical device of claim 1, wherein the numerical range of reference data is determined by collecting data from medical tests performed on a number of patients.

* * * * *